United States Patent [19]

Grimberg

[11] Patent Number: 5,229,132
[45] Date of Patent: Jul. 20, 1993

[54] NON-ABSORBABLE GASTROINTESTINAL MEDICAMENT PROVIDED FOR TREATING THE TWO LEVELS OF THE DIGESTIVE TRACT AT THE SAME TIME

[76] Inventor: Georges S. Grimberg, 123 rue de l'Université, 75007 Paris, France

[21] Appl. No.: 371,675

[22] Filed: Jun. 23, 1989

Related U.S. Application Data

[63] Continuation-in-part of Ser. No. 830,259, Feb. 14, 1986, abandoned.

[30] Foreign Application Priority Data

Feb. 22, 1985 [FR] France ................. 85 02623

[51] Int. Cl.$^5$ ................................. A61K 9/64
[52] U.S. Cl. ........................... 424/456; 424/464
[58] Field of Search .............. 424/452, 456, 457, 458, 424/459, 463, 490, 464, 469, 474

[56] References Cited

U.S. PATENT DOCUMENTS

| | | | |
|---|---|---|---|
| 2,738,303 | 3/1956 | Blythe | 424/458 |
| 4,173,626 | 11/1979 | Dempski et al. | 424/497 |
| 4,310,660 | 1/1982 | Birkenmyer | 514/24 |
| 4,342,757 | 8/1982 | Christensen et al. | 514/201 |
| 4,459,295 | 7/1984 | Higuchi et al. | 524/40 |
| 4,574,080 | 3/1986 | Roswall et al. | 424/458 |
| 4,578,264 | 3/1986 | Stricker et al. | 424/462 |
| 4,713,247 | 12/1987 | Sakamoto et al. | 424/462 |

FOREIGN PATENT DOCUMENTS 0103991 3/1984 European Pat. Off. .

OTHER PUBLICATIONS

Physician's Desk Reference, PDR 33 Edition 1979, 1384.

*Primary Examiner*—Thurman K. Page
*Assistant Examiner*—Leon R. Horne
*Attorney, Agent, or Firm*—Browdy and Neimark

[57] ABSTRACT

A non-absorbable and soluble gastrointestinal medicine provided for treating the two levels of the digestive tract, i.e. the stomach and the intestines. The medicine is presented in a gastroresistant oral pharmaceutical form associated with a non-enterically-coated oral pharmaceutical form.

2 Claims, 1 Drawing Sheet

NON-ABSORBABLE GASTROINTESTINAL MEDICAMENT PROVIDED FOR TREATING THE TWO LEVELS OF THE DIGESTIVE TRACT AT THE SAME TIME

This application is a continuation-in-part, of application Ser. No. 06/830,259, filed Feb. 14, 1986, now abandoned.

FIELD OF THE INVENTION

Some diseases of the digestive tract are difficult to localize. The symptoms are wide and very often, the stomach and the digestive tract are concerned.

BACKGROUND OF THE INVENTION

If one considers the medicines which are not absorbed by the human system, that is medicines swallowed and evacuated by the digestive tract without entering the blood, their action at various stages of the digestive tract can only take place if this action is not used up by a preceding stage.

In the case of insoluble medication, i.e., absorbents such as activated carbon and simethicone ((trimethylsilyl)-omega-methylpoly [oxydimethylsilylene] mixed with silicon dioxide), are released at the stomach level quickly, with the result that most absorption sites become occupied. Thus, the medication quickly loses its effectiveness before passing into the intestine.

To alleviate these difficulties, manufacturers have provided non-absorbable, gastro-insoluble medications in a package of two dosage forms. One capsule in the package is enterically coated so that the capsule dissolves only in the intestine, while the other capsule dissolves only in the stomach, thus releasing its medication. Carbosilane (a product of the present Assignee, which comprises one enterically-coated capsule of charcoal mixed with simethicone and one non-enterically-coated capsule of the same medication) and Phazym (one enterically-coated capsule of simethicone with one non-enterically-coated capsule of simethicone) are two examples of such medications.

Soluble, non-absorbable, gastro-resistant oral medications are used for treating conditions localized with the gastro-intestinal tract. The medications include some antibiotics, antispasmodics, enzymes, antacids, antimitotics, etc. Unlike insoluble gastrointestinal medications, these substances do not depend on surface area and surface absorbancy for their activity. Accordingly, soluble gastro-resistant oral medications are free of the aforementioned difficulties experienced with gastro-insoluble oral medications. For that reason, those skilled in the art have not considered the possibility of obtaining improved results by providing an enterically coated capsule of a gastro-resistant soluble oral medication with a non-enterically coated capsule of the same medication.

Although gastro-sensitive medications (such as injectable penicillin) and medications which irritate the stomach and may not be used therein have been provided in enterically coated form, no need had been seen for enterically-coated gastrosoluble gastro-resistant medications (i.e., medications which are soluble in and not destroyed by gastric juices) which do not significantly irritate the stomach and which indeed are intended for use therein. Accordingly, a combined dosage form of a gastro-resistant, non-absorbable oral medication in enteric and non-enteric capsules was not previously envisioned.

Yet, as applicants have observed, where a gastro-resistant medicine is soluble, it may be diluted within the stomach before it passes into the intestine. Accordingly, where both the stomach and intestine are to be treated with the same soluble (in the digestive system) gastro-resistant medication, previous medical practice required the administration of a single oral dose, which, upon dilution and use within the stomach, remained at sufficient strength to exhibit useful activity within the intestine. Such large dosages can significantly increase both the occurrence of side-effects and the expense of a medication.

OBJECTS AND SUMMARY OF THE INVENTION

Therefore, the object of the present invention is to provide a soluble-gastro resistant medicine, non absorbable by the human system and permitting a treatment at each of the levels of the digestive tract due to the fact that the first level of the digestive tract (the stomach) receives a certain quantity of medicine which exfoliates very quickly, then the second level of the digestive track (the intestines) receives another quantity of medicine, but this latter quantity of medicine is protected either by an enteric-coating.

According to the invention, the non-absorbable soluble gastrointestinal medicine, provided for treating two levels of the digestive tract, is characterized in that it is presented in an enterically-coated capsule form associated with a uncoated non-enterically-coated pharmaceutical capsule form.

Surprisingly, improved efficacy has now been found to occur with gastric soluble, non-absorbable gastro-resistant oral medications provided in the form of a pharmaceutically effective amount (for treating the stomach, i.e., gastro-therapeutic) of the chosen medication in one non-enterically coated dose combined with a pharmaceutically effective amount (for treating the intestines, i.e., intestinally therapeutic) amount of that same medication within an enterically-coated dose.

Various other features of the invention will become more apparent form the following detailed description and examples given for supporting the invention.

DETAILED DESCRIPTION OF THE INVENTION

Useful medications which may be administered according to the present invention include kanamycin (kanamycin A, B or C or mixtures and derivatives thereof), neomycin B, hydrochloride, framycetin, vanomycin, polymyxin B, colistin, paromycin and chlorhexidine. These medications and their characteristics are well known. The enterically coated part of the medication according to this invention should contain an amount of the medication which provides a therapeutically useful concentration in the intestine. The uncoated portion of the medication should contain an amount of medication which provides a therapeutically useful concentration within the stomach. Because the effective concentrations of antibiotics and the volume of liquids typically found within the intestines and stomach are generally well-known, those skilled in the art can determine appropriate dosages for both the coated and uncoated portions of the galenic form according to the present invention without undue experimentation.

Figure 1:
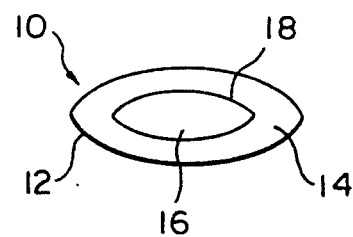
FIG. 1 is a cross-sectional view of a first embodiment according to the present invention.

The medication according to the present invention can be supplied in several forms. In FIG. 1, a tablet 10, with an outer gastrosoluble layer 12, generally made of sugar, is provided. An outer layer of therapeutic agent 14 is quickly released into the stomach as the tablet exfoliates by virtue of the dissolution of layer 12. The inner layer of medicament 16, however, is enterically coated, for example by a shellac or polyvinylpyrrolidone layer 18 and is thus released into the intestines only.

Figure 2:
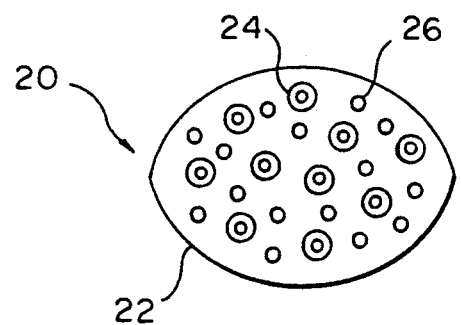
FIG. 2 is a cross-sectional view of a second embodiment according to the present invention.

In FIG. 2, a tablet 20 has a gastrosoluble outer coating 22 of, for example, sugar, enclosing enterically coated (i.e., microencapsulated) and uncoated particles of active therapeutic agent, 24 and 26, respectively. Encapsulated and non-encapsulated particles can also be enclosed within a gelatin capsule.

Figure 3:
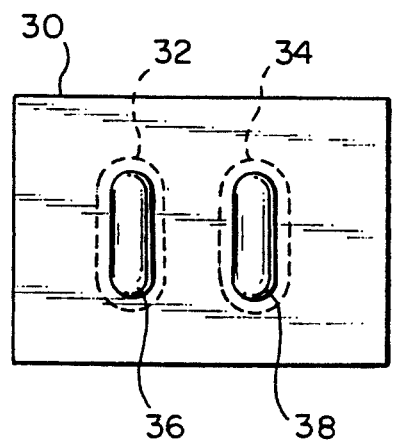
FIG. 3 is a plan view of a third embodiment according to the present invention.

Sometimes the required dosage of active therapeutic agent will be too large to permit comfortable swallowing of a single tablet or capsule containing the entire intestinally and gastro-therapeutic dose. In those case, the dosage form illustrated in FIG. 3 is especially useful. A blister package 30 contains two blisters, 32 and 34, containing and enclosing therein capsules 36 and 38, respectively, of active therapeutic ingredients. Capsule 36 is a standard gel capsule containing a gastro-therapeutic unit dose of the therapeutic agent, but capsule 38 (which contains an intestinally effective unit dose of the therapeutic agent) is enterically coated or contains enterically coated particles of the therapeutic agent. When the patient takes the dose of medication, he breaks open the blisters and swallows both capsules at the same or essentially the same time. If desired, blister package 30 can be joined with other blister packages of the same construction, via perforated lines at the edges of each blister package, to form a board containing several doses of the dosage form of FIG. 3. Whenever desired, a single blister package can then be torn from the board.

The embodiment of FIG. 3 also reduces costs, since microencapsulation or multi-layering becomes unnecessary. Further, rather than capsules, the blisters of the FIG. 3 dosage form can contain tablets or similar forms of active ingredient.

If, for example, Simethicone is taken, it is found that if 100 mg of Simethicone are given to the human system in a non-enterically-coated capsule, the action on the patients is notably less than that obtained with 50 mg of Simethicone in a non-enterically-coated capsule form plus 50 mg of Simethicone in a an enterically-coated capsule form; these two capsules being taken at the same time.

This superior result, obtained by the prior art, has been checked on patients exhibiting various symptoms such as: meteorism, emission of gases via the anus, eructations, slownesses of the digestion, postprandial drowsiness, feeling of discomfort after the meals.

Each of these symptoms has been marked from 0 to 3 according to its intensity; inexistent: 0; slight intensity: 1, medium: 2; marked: 3.

This quantification has been made by the patient and checked by the experimentor.

For control purposes, two sorts of products were administered:
Product A: non-enterically-coated capsule of Simethicone,
Product B: non-enterically-coated capsule of Simethicone.

The patients having been divided into two groups (I and II) of 50 patients, each of them has taken:
Group I: two 50 mg capsule of product A, thrice daily
Group II: one 50 mg capsule of product A along with one 50 mg capsule of product B, thrice daily.

The duration of the treatment has been 15 days $(T_0-T_{15})$.

The score difference for each patient between time $T_0$ and time $T_{15}$ has permitted studying the two groups of patients.

The result is a difference statistically significative between the two groups.

Group II, that is the group having taken product A + product B is superior in result to group I, that is the group having taken product A + product A.

Further experimentations have shown that the improved efficacy is virtually the same with medicinal coal and, surprisingly, with gastroresistant soluble oral medications.

EXAMPLES

In a more detailed manner, the following examples are provided:

EXAMPLE 1

| | two separate capsules | |
| --- | --- | --- |
| | Capsule A (enterically-coated) | Capsule B (no enteric coating) |
| kanamycin sulfate | 0.250 g | 0.250 g |

Capsules A and B are placed with adjacent blisters on a blister pack.

EXAMPLE 2

| | single capsule without enteric coating |
| --- | --- |
| kanamycin sulfate | 0.250 g |
| enterically-coated kanamycin sulfate | 0.250 g |

Non-absorbed and non-soluble substances include: nifuroxazide, iodoquinol and bismuth salts.

The following illustrates a dosage form suitable for the administration of bismuth.

| | Capsule A (enterically-coated) | Capsule B (no enteric coating) |
| --- | --- | --- |
| ammonium colloidal bismuth citrate | 150 mg | 150 mg |

Capsules A and B are placed within adjacent blisters on a blister pack.

What is claimed is:

1. A method for treating, in sequence, the stomach and the intestines of a patient with a medicament consisting essentially of a non-absorbable, soluble gastrointestinal medication selected from the group consisting of kanamycin A, kanamycin B, kanamycin C, and mixtures and derivatives thereof; neomycin B hydrochloride; framycetin; vanomycin; polymixin B; colistin, paromycin; and chlorhexidine;

comprising administering to a patient in need thereof an orally administrable dosage form consisting essentially of a first capsule of a therapeutically effective amount of said medicine, which first capsule exfoliates at a first level of the digestive tract, along with a second capsule of a therapeutically effective amount of said medicine, which second capsule protects said medicine so that said medicine may be received at a second level of the digestive tract beyond the level of the stomach;

said first and second capsules being administered simultaneously.

2. In a method for treating the stomach and intestines of a patient with a medicament consisting essentially of a nonabsorbable, soluble gastrointestinal medication selected from the group consisting of kanamycin A, kanamycin B, kanamycin C, and mixtures and derivatives thereof; neomycin B hydrochloride; framycetin; vanomycin; polymixin B; colistin; paromycin; and chlorhexidine;

the improvement comprising administering to a patient in need thereof an orally administrable dosage form consisting essentially of a first capsule of a therapeutically effective amount of said medicine, which first capsule exfoliates at a first level of the digestive tract, along with a second capsule of a therapeutically effective amount of said medicine, which second capsule protects said medicine so that said medicine may be received at a second level of the digestive tract beyond the level of the stomach;

wherein said first and second capsules are administered simultaneously.

* * * * *